US011393555B1

(12) United States Patent
Russo et al.

(10) Patent No.: US 11,393,555 B1
(45) Date of Patent: Jul. 19, 2022

(54) DYNAMIC COORDINATING FRAMEWORK FOR MODEL CELL SIMULATIONS

(71) Applicant: X Development LLC, Mountain View, CA (US)

(72) Inventors: Frank Russo, Sunnyvale, CA (US); Jason Thompson, Redwood City, CA (US); Nicholas Ruggero, Menlo Park, CA (US)

(73) Assignee: X Development LLC, Mountain View, CA (US)

( * ) Notice: Subject to any disclaimer, the term of this patent is extended or adjusted under 35 U.S.C. 154(b) by 955 days.

(21) Appl. No.: 16/123,877

(22) Filed: Sep. 6, 2018

(51) Int. Cl.
*G16B 5/00* (2019.01)

(52) U.S. Cl.
CPC ..................... *G16B 5/00* (2019.02)

(58) Field of Classification Search
None
See application file for complete search history.

(56) References Cited

U.S. PATENT DOCUMENTS

| 5,930,154 | A | 7/1999 | Thalhammer-Reyero |
| 2004/0029149 | A1 | 2/2004 | Palsson et al. |
| 2007/0005317 | A1 | 1/2007 | Paxson et al. |

FOREIGN PATENT DOCUMENTS

| WO | 2000-65523 A1 | 11/2000 |
| WO | WO 2014/015196 A2 | 1/2014 |

OTHER PUBLICATIONS

Tomita, Masaru, et al. "E-CELL: software environment for whole-cell simulation." Bioinformatics (Oxford, England) 15.1 (1999): 72-84.*

Andrews, Steven S. "Serial rebinding of ligands to clustered receptors as exemplified by bacterial chemotaxis." Physical biology 2.2 (2005): 111.*
Andrews, Steven S., and Dennis Bray. "Stochastic simulation of chemical reactions with spatial resolution and single molecule detail." Physical biology 1.3 (2004): 137.*
Masaru, et. al., "The E-Cell Project", Recomb 2000., Proceedings of the 4th Annual International Conference on Computational Molecular Biology, Tokyo, JP, Apr. 4-11, 2000, all pgs.
International Application No. PCT/US2019/046990, International Preliminary Report on Patentability, dated Mar. 18, 2021, 9 pages.
International Application No. PCT/US2019/046990, International Search Report and Written Opinion Received, dated Dec. 9, 2019, 13 pages.

* cited by examiner

*Primary Examiner* — G Steven Vanni
(74) *Attorney, Agent, or Firm* — Kilpatrick Townsend & Stockton LLP (57) ABSTRACT

A method for allocating resources among multiple sub-models in a simulation of a biological cell is described herein. The method receives an initial state dataset including initial aggregate resources in a plurality of sub-models, which make up a whole cell model. The method calculates, at a first time step, an outcome of each of the sub-models, which includes a local production, a local consumption and local net value of at least one resource shared between at least two sub-models. The method calculates a subsequent state dataset based on the outcome of each of the sub-models. The subsequent state dataset includes subsequent aggregate resources, the local production, the local consumption and local net value. The method determines, at a second time step, a second outcome of each of the plurality of sub-models based on the subsequent aggregate resources and the local production, local consumption and local net value.

10 Claims, 5 Drawing Sheets

DYNAMIC COORDINATING FRAMEWORK FOR MODEL CELL SIMULATIONS

BACKGROUND

Field of Art

This description generally relates to coordinating between sub-models of a model system of a cell, and specifically to apportioning common resources to sub-models that operate independently.

Description of the Related Art

A model system of a whole cell may be made up of hundreds of molecules, whose relationships may be divided between any number of sub-models, which each have connecting relationships and reactions that link between each sub-model. Dividing a linked network into a number of sub-models allows each sub-model to be built on different mathematical frameworks. For example, a first sub-model may be constructed from partial differential equation (PDE) relationships, whereas a second sub-model may be constructed from mass-balance constraints. However, dividing a model system into different sub-models often poses difficulties, since resources common to the various sub-models (such as ATP, enzymes and proteins) are distributed to each of the various sub-models. Determining how to coordinate production and consumption of common resources between sub-models may become difficult.

SUMMARY

A biological cell's functions and structure can be conceptualized as a model system of linked sub-models that operate together to simulate behavior of a whole cell. The whole cell can thus be broken down into various linked macro-level functions, including the process of cell metabolism, the generation of physical elements like cell walls and membranes, the processes of transcription and translation, the generation of proteins and other macromolecules, etc. Each of these macro-level functions may be modeled by different sub-models. Cell resources, such as molecules, are distributed across the various sub-models of a whole cell. A state dataset described herein coordinates the use of common resources among sub-models of a whole cell.

A method for allocating resources among multiple sub-models in a simulation of a biological cell is described herein. The method receives an initial state dataset including initial aggregate resources in a plurality of sub-models. The plurality of sub-models make up a whole cell model. The method calculates, at a first time step, an outcome of each of the plurality of sub-models. The outcome includes a local production, a local consumption and local net value of at least one resource shared between at least two sub-models. The method calculates a subsequent state dataset based on the outcome of each of the plurality of sub-models. The subsequent state dataset includes subsequent aggregate resources, the local production, the local consumption and local net value. The method determines, at a second time step, a second outcome of each of the plurality of sub-models based on the subsequent aggregate resources and the local production, local consumption and local net value.

DETAILED DESCRIPTION OF DRAWINGS

I. Context

A cell's functions and structures can be translated into a linked network of pathways between reactants and products that together form a model system of the cell. The linked network can be structured on several different levels. At a baseline level, the linked network is a reaction network of molecule nodes, process nodes and edges linking the molecule nodes to the processes in which they participate. In a mass balanced model, a constraint is placed at each node that requires that a net input flux of a molecule match a net output flux, e.g., that mass cannot be consumed or produced. The mass balance requirement allows for a number of mathematical simplifications, but also means that input and output fluxes of molecules at higher levels of the model (such as the sub-models) are major parameters for regulating and determining sub-model behavior, since they are connected to a foundational constraint of the network.

Dividing the linked network into a number of sub-models has many benefits. Certain biological processes are better modeled using different algorithms (such as PDEs, ordinary differential equations (ODE)s, flux balance analysis (FBA), other numerical methods, etc.) and dividing the full network into different types of models allows each sub-model to better match biological behavior. Additionally, the different sub-models allow for segmentation of the whole cell model, such that each sub-model operates independently. However, dividing the linked network into sub-models means that finite, global cell resources, such as ATP, enzymes and proteins, have to be allotted to the various sub-models. During a single simulation of the cell, as sub-models are run for each time step, coordinating between independent sub-models becomes difficult, since a single sub-model may fully deplete or monopolize a molecule, preventing other sub-models from functioning. This is particularly problematic for molecules with high "throughput" i.e., rates of production and consumption in the network, since a small perturbation in the amount of these molecules can quickly lead to full depletion, affecting numerous sub-models. Previous solutions to such distribution problems generally (independent of this cell-based context) have focused on building a "master" distribution algorithm, which doles out resources to the various sub-models through its own internal calculation. However, this is not an ideal solution because it does not reflect the biological reality of the cell, requires additional computation, and often leads to artifacts in the whole cell model as a result of the chosen distribution algorithm.

A state dataset is used to coordinate the distribution of common molecules across multiple sub-models within a whole cell model. The state dataset aggregates production, consumption, and net "amount on hand" for all molecules across all sub-models of the whole cell model, as well as stores these metrics per sub-model. The state dataset may convert these metrics to any intrinsic or derivable units, such as molecule counts, grams, moles, pH, etc. depending on which units are most useful to each sub-model. For example, one sub-model may have a maximum pH level associated with it, in which case it may request pH values from the state dataset, whereas another sub-model may be primarily built from an algorithm based on molecule count calculations, in which case the pH level may not be relevant.

For each time step of a simulation, the state dataset is updated with the outcomes of each sub-model. The next time step is calculated from the outcome of the previous one, as stored and retrieved from the state dataset. Production and consumption in each sub-model are calculated from aggregate metrics (e.g., the total amount on hand, production, and consumption in the whole cell) and the sub-model's own metrics from a previous time step. Thus each sub-model "sees" only the total behavior and its own past behavior, and doesn't "know" about other sub-models through anything other than the aggregate metrics. Based on the sub-model's own past behavior and the aggregate behavior, the sub-model calculates its production and consumption for the next time step. Thus, if as a result of a previous time step, a net of 100 molecules of ATP are available, and the sub-model consumed 50 and produced 10,000, the sub-model's behavior in the next time step will reflect the fact that the sub-model was the primary producer of ATP, and its production and consumption may be proportional to the previous time step's.

By calculating each sub-model's behavior from a previous time step, the scenario in which a sub-model depletes a molecule can be avoided, since a sub-model that is a primary producer of a molecule can't easily be switched to becoming a primary consumer. Additionally, by keeping track of both production and consumption, rather than combining these rates to a single delta measurement, the mass balance constraint of the model can be used to help determine sub-model behavior. The state dataset framework eliminates the need for a master allocation algorithm, allowing each sub-model to independently determine its next behavior and effectively distribute resources based on aggregate and local production and consumption.

A benefit that flows from this is that the simulation data produced as an output of the model cell is more likely to be reflective of the biology of the cell being modeled, rather than a distorted view of that biology that would otherwise be introduced through use of a master allocation algorithm. Removing the possibility for this distortion increases the correct-ness and therefore trust in the simulation data, meaning that on average less in silico simulations will need to be performed in order to reliably estimate the behavior of the model cell, thereby reducing computer processing requirements (both in time to run and memory used by the resulting simulation data), and reducing the amount of data that needs to be considered in order to transition from in silico simulation to in vitro or in vivo evaluation of cellular pathways or targets of interest in relation to the model cell. For example, if a master allocation algorithm were used, some number X of simulations (producing X datasets) may be needed to evaluate the model cell while accounting for biases that may be introduced by the master allocation algorithm. Through the methods and systems herein, some lesser number Y (X>Y) simulations may be needed instead, thereby producing Y datasets. All else equal, identifying discoveries or errors in the simulation/experiment is easier using Y datasets than X datasets. As a specific example, the output of a given simulation may directly inform whether a follow-on simulation should be performed. As a specific example, detected bias in the simulation data as a result of the presence master allocation algorithm may indicate the need for a follow-on simulation to adjust for such a detected effect.

Furthermore, the sets of simulation data produced by multiple simulations of a model cell (e.g., either X or Y as above) may provide some parameter space which is to be interrogated in vitro or in vivo in a web lab (e.g., using cell cultures). This may be the case, for example, for target identification or compound (hit) evaluation for a drug discovery process. Reducing the number of in silico simulations and resulting number of datasets produced by the simulations may then correspond to a reduction of the parameter space of the web lab tests. Wet lab tests are costly in terms of employee time, physical resources required, physical space, and so on. Any reduction in the parameter space of wet lab evaluation would generate tangible benefits in this regard.

Additionally, this technique may be useful for experiment design in a situation where users may run the simulations in silico first and perform only those experiments that include potentially new discoveries in vitro or in vivo in order to save time and laboratory resources. The use of a master allocation algorithm creates an additional "point of failure" that can make it more difficult to determine whether the simulation data indicate an error in the simulation, or a potential new discovery.

Generally, the capability to effectively simulate a model cell in silico allows an operator to carry out experiments more quickly and cost-effectively relative to carrying out those experiments in an in vitro or in vivo manner. A general goal of many such experiments involve running a simulation of a model cell to determine how the model cell's state will change over the course of the simulation under a given set of environmental conditions including not only variables such as temperature, but also in the presence of perturbations such as molecular compounds of interest. Examples of experiments that can be carried out through simulation with a model cell include, but are not limited to: evaluating the impact of proposed gene knockouts, small molecules, biologic compounds, cell environment changes, or other perturbations on the growth, gene expression, or other property of a model cell; screening multiple drugs, compounds, or other perturbations to identify perturbations effective at achieving a desired result; screening multiple drugs, compounds, or other perturbations for off-target effects such as for problems with toxicity; predicting whether a given model cell will grow or not under a given set of conditions; predicting the phenotype of a given model cell, calculating the expected product yield of a model cell; identifying new possible targets to achieve a desired therapeutic effect, evaluating the behavior of novel synthetic compounds (such as proteins) or entire artificial cells; evaluating the impact of known pharmaceuticals in different model cells (e.g., non-human cells for animal treatment, etc.); screening a model cell under multiple media conditions to identify genes to target for knockout or modification for use in identifying antibiotic compounds to apply to those genes; and evaluating the productivity or yield of amino acids or other genetic or cellular products produced by the model cell to determine environmental conditions or applicable compounds that might improve productivity or yield.

With a model cell, any of the examples above can be run in singular or in plural. For example, the effect of a single gene knockout on RNA transcription may be evaluated on a single model cell. Alternatively, the effect of multiple different gene knockouts may all be evaluated against the single model cell. Thus, the operator can simulate hundreds (or more) of potential gene knockout experiments to identify which gene knockouts yield favorable results. From there, the operator can perform the identified subset of experiments in vitro or in vivo, saving the effort of performing the other hundreds of experiments in vitro or in vivo. If one of the in vitro or in vivo experiments proves favorable, therapeutics directed to that particular gene knocked target can be explored. This principle extends to the other example, for example hundreds (or more) potential compounds to up or down regulate a given target may be screened by running simulations of the model cell assuming presence of the potential compounds to identify which compounds yield favorable results. From there, the operator can perform the identified subsets of experiments in vitro or in vivo, saving the effort of performing the other hundreds of experiments in vitro or in vivo. The model cell is also advantageous because it may provide information about compound toxicity that would save or reduce the cost and time associated with animal studies for the purpose of meeting regulatory requirements for providing the compound to a patient population.

Additionally, another benefit of simulating model cells is that a simulation allows for the analysis of the dynamics of state changes within the model cell at much higher time resolution and across a much more comprehensive set of variables than is possible in any wet lab experiment. This would an operator to, for example, examine the interaction between an immune cell and its target, and a range of possible perturbations to that interaction, in a way that would not be tractable given any amount of wet-lab work.

I. SIMULATION MODEL OF A SIMULATION

Figure 1:
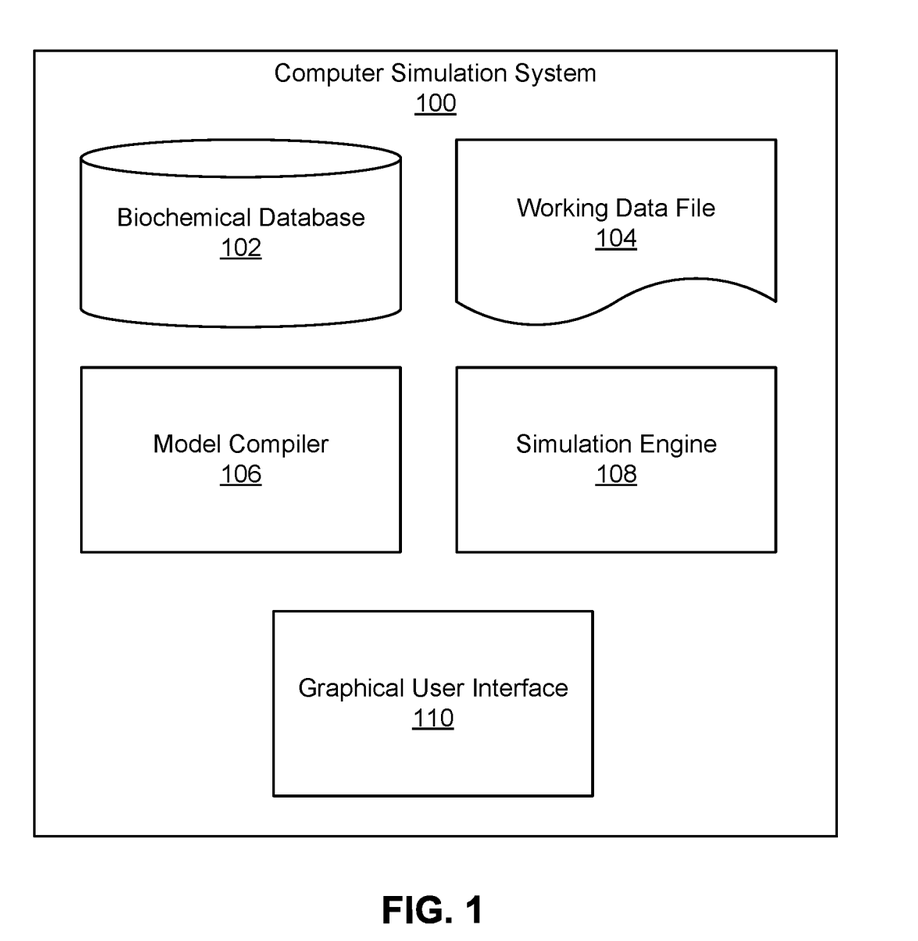
FIG. 1 is a block diagram illustrating computation components of a simulation system for modeling the behavior of a biological cell, according to one embodiment.

FIG. 1 is a block diagram illustrating computational components of a computer simulation system 100 (herein referred to as simply "simulation system") for modeling the behavior of a biological cell, in accordance with an embodiment. Depending on the embodiment, each component of the simulation system 100 may be implemented on one or more servers or other computational devices that are configured to communicate over a network (e.g. the Internet, a local area network, etc.). Alternatively, all computational components may be locally present on a single computational device. The computational components making up the simulation system 100 shown in FIG. 1 are a biochemical database 102, a working data file 104, a model compiler 106, a simulation engine 108, and a GUI 110.

Figure 2A:
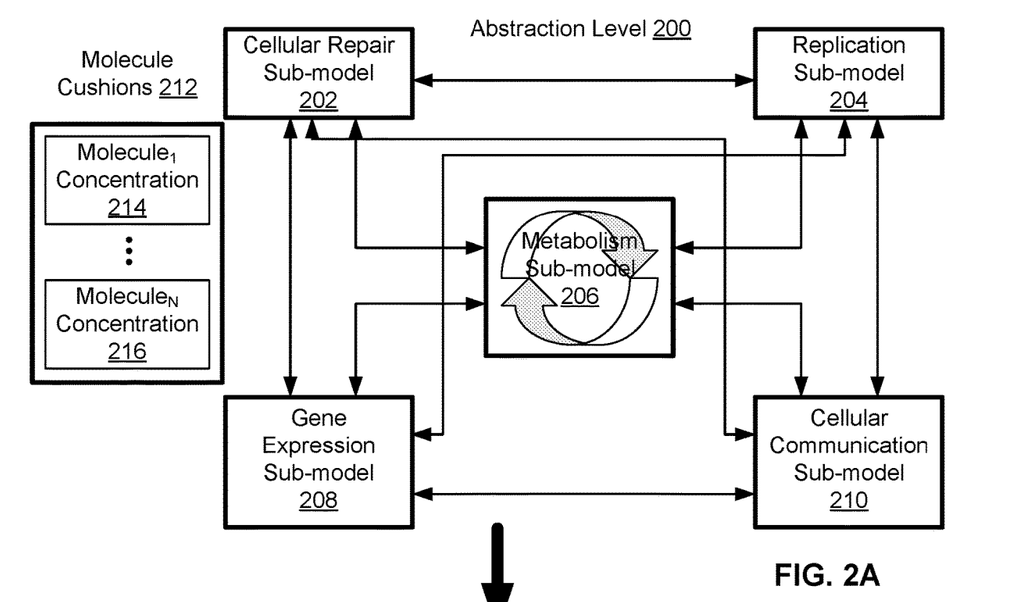
FIG. 2A is a block diagram of an abstraction level of a whole cell model, according to one embodiment.

The biochemical database 102 is a database that stores data regarding molecules and processes that may be present or may occur in a biochemical environment simulated using the simulation system 100. The biochemical database 102 stores compositional data for each molecule that may be of use in the simulation, as well as data specifying how each molecule may be involved in one or more processes simulated by the simulation system 100. The biochemical database 102 may, more specifically, include information describing an organism at various levels of specificity. For example, on a more detailed level, the biochemical database 102 includes a catalog of an organism's genes, transcripts, proteins, etc. At a higher level of generality, the biochemical database 102 may include structures such as an organism's protein complexes. Although any database structure may be used to implement the biochemical database 102, in one embodiment the biochemical database 102 is implemented as a bipartite reaction network, which is described in further detail with reference to FIG. 2. Those of skill in the art will recognize that the same biochemical could be stored in another type of data structure.

The working data file 104 (sometimes referred to as the working file) is a set of instructions for configuring the simulation system 100. The simulation system 100 may be configured to simulate a single set of molecules and processes and, therefore, is not configured separately for each use of simulation system 100. Alternately, the working file 104 is used to select the molecules and processes to be simulated in the simulation system 100, and is therefore configured separately for each use of the simulation system 100. Additionally, the working file 104 may designate the specific cell functions to be modelled as well as the models to be included in the simulation system 100. Furthermore, the working file 104 may include parameters for one or more sub-models included in the simulation system 100, as well as a set of initial conditions for each of those models.

The model compiler 106 uses working file 104 to compile the simulation system 100 so that simulations can be run. The model compiler 106 accesses the data retrieved from the biochemical database 102 and the working file 104 to generate various components of each simulation, examples of which include but are not limited to: a stoichiometric matrix, a bipartite network link molecule and process nodes, initial flux vectors that describe the rate of production and/or consumption of molecules, and quantities prior to a model being run for the first iteration, an objective function for each model, and any constraints on any of the models. After processing the various components of the simulation, the model compiler 106 outputs a simulation configuration data file (sometimes referred to as a configuration file or simconfig file). The configuration file is an input to the simulation engine 108 to generate a simulation of the cellular process described by the working file 104. In some implementations, the configuration file is a set of instructions to be executed by the simulation engine to accurately generate a simulation.

The simulation engine 108 manages the execution of the configuration or simconfig file produced by the model compiler 106 to simulate a biochemical process using the simulation system 100. The simulation engine 108 may initialize a given simulation using the initial conditions as constructed by the compiler 106 and as contained in the simconfig file. The simulation engine 108 creates an initial state vector, which includes the concentration of each molecule included in the simulation. The simulation engine 108 creates any initial exchange flux values into and out of each model in the simulation, which sets an initial rate of consumption and production for the associated molecules. The simulation engine 108 then iterates through a time step of the simulation, running the models of the simulation with the input state vectors and fluxes. Generally, this involves the simulation engine 108 arriving at a solution of the model for a first time step after the initial state, where the time step is of a predetermined length. A length of the time step may be determined by a state dataset, as described in further detail below. The solution for each model for that time step may include, but is not limited to, the concentrations of the molecules output by each model, the fluxes of those molecules, and any changes to the overall biochemical environment (e.g. temperature changes, pH changes, etc.) caused by the processes being simulated by each model.

After the completion of the initial time step of the simulation, the simulation engine 108 updates the initial state dataset, flux vectors, and any other relevant datasets with the output of the initial time step. As a specific example for a FBA-based sub-model, the simulation engine 108 may use the fluxes determined during the running of the models multiplied by the length of the predetermined time step to determine the new concentrations of the molecules included in the models of the simulation. The simulation engine 108 may also calculate the exchange fluxes that connect each model with each other model in the simulation. The simulation system 100 then runs a second time step of the simulation similarly to the first time step using the updated state dataset and any other parameters of the simulation. The simulation engine 108 continues this process for a number of time steps or until reaching a termination state or receiving a termination input. An example of state datasets updated across time steps of a simulation are described in further detail with reference to FIG. 4.

II. BIOCHEMICAL DATABASE

In some examples, the biochemical database 102 stores a reaction network structured as a bipartite graph. A reaction network characterizes a reaction pathway, the inputs, and the outputs of any steps occurring along the reaction pathway. The bipartite graph consists of two distinct sets of nodes, molecule and process, which are connected by edges. A bipartite graph, additionally, includes input molecule nodes representing the input molecules of the reaction. Each of the input molecule nodes is connected to at least one of the intermediary, process node or an output molecule node by one or more edges.

Within a bipartite graph structuring of a reaction network, input molecule nodes represent the first products of a reaction. Depending on the number of molecule and process nodes in the pathways of the reaction network, there may be any number of molecule nodes and edges in the reaction network. In one specific use of such a network, the output molecule nodes represent the outputs of a particular cell function (or set of cell functions) such as metabolism, and are the output boundary of the bipartite metabolic network.

A molecule node may represent small molecules such as water, carbon dioxide, protons, etc. or macromolecules such as proteins, lipids, alcohols, organic acids, vitamins, etc. A molecule node may also represent organism specific molecules such as transcripts, proteins, and protein complexes. A molecule node may contain a plurality of metadata fields to describe the molecule including the molecule name, a molecule formula, an amino acid sequence, a macromolecular structure, electrical charge, chemical or physical properties (pKa, melting point, solubility, etc.) and any component molecules. Additionally, some non-physical properties may be included in the metadata of a molecule node including drug interaction, 3D structure etc. A molecule node need not contain information for each one of the previously described metadata categories. In some examples, molecule nodes may have associated flux values. Flux values of molecule nodes represent a net rate of downstream consumption of the molecule and upstream production of a molecule. Flux values thus describe the "flow" of the molecule through a reaction network.

Process nodes describe molecular actions in a biochemical environment including but not limited to chemical reactions, regulatory interactions, binding, transport, or others. A process node includes a number of descriptive metadata fields that provide information about the process including but not limited to a list of molecules and their associated roles in the process, reaction rate information, and energy requirements for the process, sub-processes that may be involved in the process, or other more detailed information.

In alternate embodiments, the biochemical database 102 may store information describing cellular processes using a different representation from the bipartite representation example above. For example, a transcription sub-model modeling cell transcription may use transcripts and relative concentrations to construct a monomial distribution sampled at various time steps or sequence composition techniques to translate the sampled set of transcripts into an analysis of nucleoside triphosphate demand, for which a bipartite reaction network would be less useful than other representations.

III. WHOLE CELL MODEL ARCHITECTURE

FIG. 2A is a block diagram of an abstraction level 200 of a whole cell model, according to one embodiment. The abstraction level 200 of the whole cell model demonstrates the de facto relationships between sub-models of the whole cell model that are generated by an implementation level 220 of the same whole cell model, which is discussed below with reference to FIG. 2B. The abstraction level 200 of the whole cell model is thus the "view" of the whole cell model that is seen by a user interacting with the whole cell model, or any processor that carries out simulations of the whole cell model.

A. Whole Cell Model Overview

The whole cell model contains any number of sub-models which are connected to other sub-models and input and/or output molecules to other sub-models. As shown in FIG. 2A, the sub-models include a cellular repair sub-model 202, a replication sub-model 204, a metabolism sub-model 206, a gene expression sub-model 208, and/or a cellular communication sub-model 210. The arrows between sub-models may represent the input flux and/or output flux of molecules transferred between sub-models. For example, if the metabolism sub-model 206 is based on a FBA framework, in which mass-balance relationships between reaction and product molecules are used to solve for steady state input and output flux values, then the arrows leading into and out of the metabolism sub-model 206 may represent the FBA solution flux values. Arrows between sub-models and cellular metabolism 206 may represent the supply and demand for molecules between sub-models, or any transfer of molecules between sub-models. For example, if a cellular communication sub-model 210 has a surplus of ATP molecules, they may be transferred to a replication sub-model 204.

In addition to molecule concentrations within sub-models and cellular metabolism 206, the whole cell model 200 may include molecule cushions 212 that exist outside of the immediate system of supply and demand between the sub-models. The molecule cushions 212 represent reserves of molecules within the cellular environment. For example, molecule cushions 212 may be molecules that exist within a cell's cytoplasm, and which are available to molecular processes when needed. Molecule cushions 212 contain different reserve concentrations of different molecules. For example, a first molecule, $molecule_1$, may have a concentration of $molecule_1$ concentration 214. If $molecule_1$ is a molecule that has a large flux value or demand within the system of sub-models, then the reserve concentration of $molecule_1$ may be larger than other molecules with smaller demand. Thus the concentration of molecules within molecule cushions 212 may be proportional to the flux value associated with the molecule in cellular metabolism, the aggregate demand for the molecule across sub-models, and/or any other measurement of demand within the whole cell model. The molecule cushions 212 ensure that sudden increases in demand for a molecule within the whole cell model 200 do not result in complete depletions of a molecule within the whole cell model 200.

There may be any number of molecules within molecule cushions 212. A total of N molecules, represented by molecule$_N$ concentration 214, are assigned reserve concentrations within molecule cushions 212. In some examples, all molecules within the whole cell model are assigned reserve concentrations within molecule cushions 212. In other examples, molecules with demand and/or flux values above a threshold are assigned reserve concentrations within molecule cushions 212, such that a subset of the molecules within the whole cell model representing the primary flow of molecules are stored in molecule concentrations molecule$_1$ concentration 214 through molecule$_N$ concentration 214.

The effect of the molecule cushions 212 on the whole cell model is that the molecule cushion concentrations allow the demand for a molecule to instantaneously (e.g., for a given single time step evaluating the subunits) exceed supply without disrupting the whole cell model. This allows the production network to continue to function as a demand load is applied to the system of the whole cell model, giving the cell time to increase production of the molecule to meet the new demand.

A simulation of the whole cell model is a mathematical calculation across all sub-models of the whole cell model and associated with the same set of initial input parameters. Input parameters are variables that may be altered between simulations, and are described in further detail with reference to FIGS. 3-4. A single simulation produces a set of simulation data, which include all of the mathematical solutions to the equations describing the sub-models of the whole cell model. A simulation may iteratively solve the whole cell model 200 to produce simulation data over a time series, such that each time step is associated with a set of solutions to the whole cell model. Solutions for a single time step may be the result of a single, deterministic calculation, or a statistical mean from multiple iterations of solutions of one or more of the sub-models with the same initial conditions and at the same time step. This may be dependent on the type of equations describing each of the sub-models. For example, solutions may be determined from a single FBA analysis of a metabolic sub-model, or from 100 solutions of a sub-model modeled with a Monte-Carlo method. Simulation time steps are described in further reference to FIGS. 3-4.

To produce simulations of the whole cell model 200 across a time scale, the solutions at a first time are used as the initial conditions for a subsequent time step. Time steps in the time series may be adjusted to prevent depletion of molecule concentrations, such that at high flow rates of molecules in the whole cell model 200, the time steps are smaller than when the rates of consumption and production are reduced. A collection of simulation data from multiple simulations of a whole cell model 200 comprise an "experiment."

B. Abstraction Level

At the abstraction level 200, the sub-models, such as the cellular repair sub-model 202, the replication sub-model 204, the metabolism sub-model 206, the gene expression sub-model 208 and the cellular communication sub-model 210, each transfer molecules between each other. The sub-models transfer molecules and resources based on production and consumption of molecules within each sub-model. At an abstraction level 200, the sub-models "communicate" with each other by conveying molecules based on the local production and consumption of molecules within each sub-model. As described herein, "local production" and "local consumption" refer to the generation or use of molecules within a single sub-model. For example, in response to local over-production of ATP within the metabolism sub-model 206, the information about the overproduction of ATP may be conveyed to the gene expression sub-model 208, which may have a significant demand for ATP. In response, the excess ATP molecules may be conveyed from the metabolism sub-model 206 to the gene expression sub-model 208. Production and consumption of molecules within the full cell model at the abstraction level 200 may thus not be centralized, and each of the sub-models are able to communicate and transfer molecules between each other. This is indicated by the two-way arrows between each of the sub-molecules, as shown in FIG. 2A.

However, allowing for the direct transfer of molecules between each of the sub-models may become complicated as the number of sub-models within the whole cell model increases. In order to distribute molecules based on production and consumption across all the sub-models of the whole cell model, the whole cell model weighs the relative degree of supply and demand within each sub-model. For example, if demand for ATP is higher in the cellular communication sub-model 210 than in the gene expression sub-model 208, excess ATP molecules may be conveyed to the cellular communication sub-model 210 instead of the gene expression sub-model 208. While, at an abstraction level 200, the sub-models each have their own channels to transfer molecules with the other sub-models, de-centralizing distribution to each of the sub-models may become computationally complicated and unwieldy. The abstraction level 200 may thus not reflect the architecture of how the whole cell model is implemented. Instead, the abstraction level 200 represents a de-facto behavior of a whole cell model, in which molecules are transferred from sub-model to sub-model. The implementation level that produces the abstraction level 200 behavior is described in further detail below.

C. Implementation Level

Figure 2B:
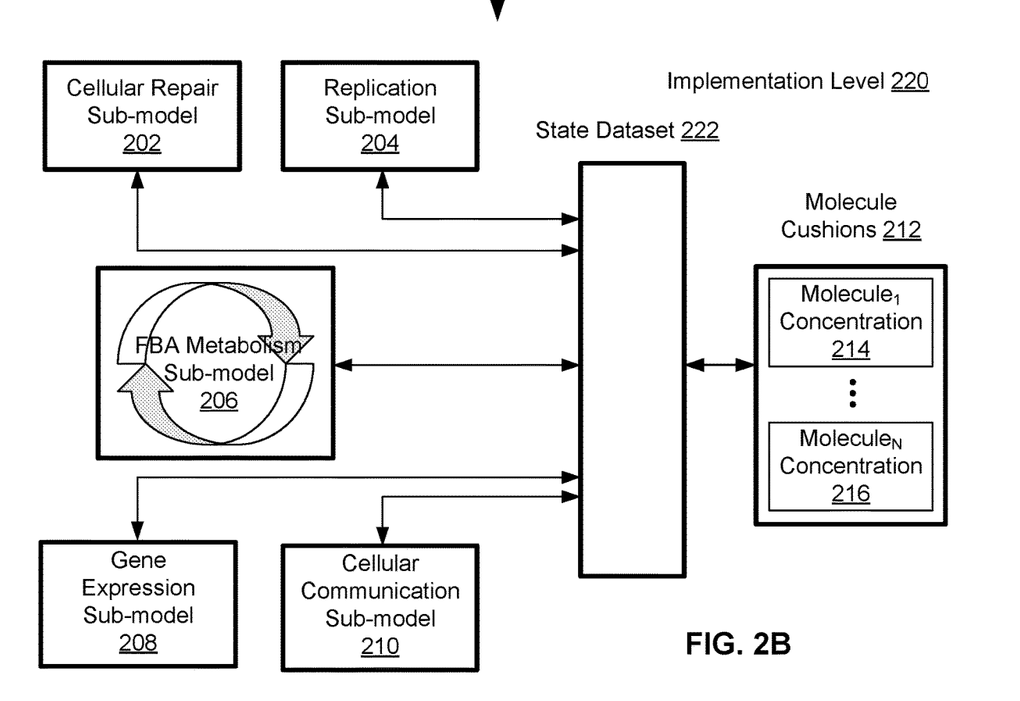
FIG. 2B is a block diagram of an implementation level of the whole cell model of FIG. 2A, according to one embodiment.

FIG. 2B is a block diagram of an implementation level 220 of the whole cell model of FIG. 2A, according to one embodiment. In order to achieve the abstraction level 200 behavior, in which molecules are exchanged between each sub-model of a whole cell model, the implementation level 220 includes a state dataset 222, which coordinates the transfer of molecules between each sub-model. Thus, while from a user perspective, each of the sub-models are connected and exchange molecules according to production and consumption within each sub-model, the whole cell model is actually structured with a coordinating state dataset 222 which as shown in the implementation level 220.

Each of the sub-models communicates with the state dataset 222, as shown by the arrows between the cellular repair sub-model 202, replication sub-model 204, FBA metabolism sub-model 206, gene expression sub-model 208 and cellular communication sub-model 210 and the state dataset 222. Each of the sub-models updates the state dataset 222 with any local changes to molecule concentrations, production or consumption of molecules, or any other parameters tracked by the state dataset 222 during each time step of a simulation. The state dataset 222 aggregates information across all of the sub-models of the whole cell model, and determines which information to convey back to each sub-model. For example, a state dataset may customize units or other parameters according to the mathematical framework used by each sub-model. For example, the state dataset 222 may provide the FBA metabolism sub-model 206 with flux values, since a FBA conception of metabolism uses flux values as a primary parameter in FBA calculations.

Elements stored within a state dataset 222 and updated by each of the sub-models are described in further detail with reference to FIG. 3-5.

Thus, at an implementation level 220, each of the sub-models in the whole cell model do not communicate directly with each other, but rather convey information about their local production and consumption of molecules to the state dataset 222. The state dataset 222 acts as a centralized pool of information about molecules across all sub-models, allowing for distribution of molecules according to relative production and consumption of molecules within each sub-model. Thus the direct transfer of molecules between sub-models shown in the abstraction level 200 is simulated at an implementation level 220 by each sub-model conveying information to the state dataset 222, which in turn distributes molecules among the sub-models. From a user perspective, however, the implementation level 220 may not be "visible" and the behavior of the whole cell model acts as if each sub-model was directly communicating with other sub-models. The process of distributing molecules to each of the sub-models of a whole cell model is described in further detail with reference to FIG. 3-5.

IV. State Dataset Components

Figure 3:
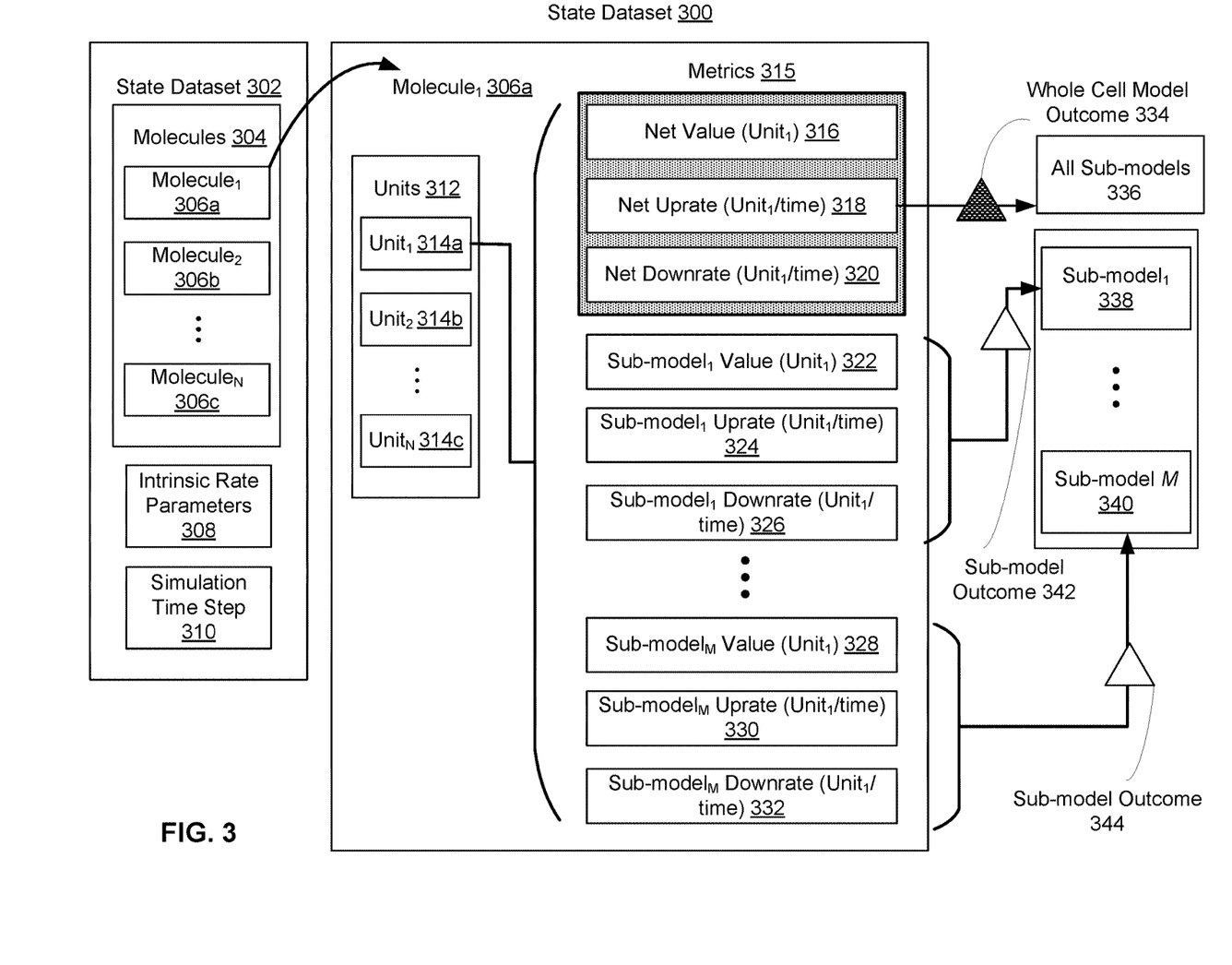
FIG. 3 is an illustration of components of a state dataset, according to one embodiment.

FIG. 3 is an illustration 300 of components of a state dataset 302, according to one embodiment. The state dataset 302 may be the state dataset 222 as shown in FIG. 2B. The state dataset 302 gathers molecule information across all sub-models of a whole cell model, such as the sub-models shown in FIG. 2B. The state dataset 302 stores both aggregate and local information about molecule production and consumption, as described below.

A. Molecules Overview

The state dataset 302 aggregates information about every molecule within a whole cell model, and stores molecule information per molecule within a portion of the dataset, molecules 304. For example, if a molecule is present in a single sub-model, it will contain a molecule entry within molecules 304. If a molecule is present in multiple sub-models, it will have a single molecule entry within molecules 304. Thus each molecule within a whole cell model is given an entry within molecules 304. For example, molecule$_1$ 306a and molecule$_2$ 306b may be present within any number of sub-models of a whole cell model. There may be any number of N molecules within a whole cell model, represented by the molecule$_N$ 306c entry within molecules 304. Each molecule entry within molecules 302 may contain a number of different metrics that measure both aggregate and local production and consumption of the molecule in the whole cell model. The information stored per molecule entry is described in further detail below.

B. Intrinsic Rate Parameters

The state dataset 302 further includes a set of intrinsic rate parameters 308. The intrinsic rate parameters 308 represent the biological limits on production and consumption of molecules. For example, a cell may not be able to instantaneously increase its rate of production to meet downstream demand due to inherent rates of cellular processes, transportation of molecules, an enzyme or facilitating molecule's limited binding rate, or any other biological rate limit that is independent of molecular concentrations. Intrinsic rate parameters 308 represent further, inherent constraints on production in addition to stoichiometric or mass balance constraints. Intrinsic rate parameters 308 are a set of time independent coefficients. As described below, intrinsic rate parameters 308 limit the "derivative" response of production or consumption, the "integral" response of production or consumption, and the "second derivative" response of production or consumption of any of the sub-models to demand outside a sub-model. Other intrinsic rate parameters 308 may limit a "proportional" response of production or consumption, or any higher order derivative responses of production or consumption.

For example, an intrinsic rate parameter is "inertia" which represents an intrinsic rate at which a sub-model can supply a molecule to a reaction. "Inertia" is a "second derivative" limit of production within a sub-model, since it represents a limit on the instantaneous, "current" rate of change of production and thus limits the rate at which the rate of change can itself adjust. "Inertia" has a damping effect on the rate at which a cell is able to produce a molecule.

A second intrinsic rate parameter is "replenishment" which represents an intrinsic rate at which a sub-model can generate supply of a molecule to meet outside demand. "Replenishment" is a form of derivative control, in that it acts on the difference between an outside rate of demand and an internal rate of consumption of a molecule. Replenishment functions as a check on upstream supply sensitivity to downstream demand.

A third example of an intrinsic rate parameter is "half-life" of a molecule, which represents an intrinsic rate of consumption of a molecule within a sub-model. "Half-life" is an "integral" limit of production, since it represents previous production of a molecule within a sub-model.

Intrinsic rate parameters may be defined for each molecule within a sub-model, such that each molecule has its own "inertia," "replenishment," and "half-life" or any other defined intrinsic rate parameters that reflect the biological limitations of using the molecule as a reactant in a chemical reaction. In some examples, different intrinsic rate parameters applied to the same molecules may be used for different sub-models. For example, the same molecule within the gene expression sub-model 208 may have a different set of intrinsic rate parameters than the cellular repair sub-model 202. In some examples, the same set of intrinsic rate parameters is used for the same molecules in all sub-models of a whole cell model. In this example, the intrinsic rate parameters 308 are "global variables" and apply to molecules across all sub-models. The intrinsic rate parameters are used to determine production and consumption of molecules within the sub-models of a whole cell model.

C. Simulation Time Step

The state dataset 302 further includes a simulation time step 310. The simulation time step 310 defines the period of time between iterative solutions of the equations of a whole cell model within a simulation of a whole cell model. The role of the simulation time step 310 in a simulation of a whole cell model is illustrated with respect to FIG. 4. The simulation time step 310 may be initialized to an initial time step. In some examples, the simulation time step 310 may be initialized to one second, however, in practice the time step may be orders of magnitude different from this depending on the system being modeled and the dynamics at play in that simulation. Generally, the time step is chosen so as to be shorter than the amount of time it takes information to propagate through the system. This could span many orders of magnitude and depends on the biological system being simulated. Preferably, the simulation data output by the simulated system should be result of a causal chain of events in the modeled system and not an artifact of the time step chosen.

In some examples, the simulation time step 310 may be constant throughout a simulation of a whole cell model. In some examples, the simulation time step 310 is dynamic, and is adjusted in response to fluctuations in molecule concentrations during a simulation of a whole cell model. In these examples, the simulation time step 310 may be increased in response to molecule concentrations within sub-models remaining above a threshold between previous time steps (e.g., remaining above zero). In some examples, the simulation time step 310 may be increased in response to a molecule's net concentration across all sub-models of a whole cell model remaining above a threshold. In some examples, the simulation time step 310 may be increased in response to a constant concentration of all molecules within the molecule cushions 212. In some examples, the simulation time step 310 may be increased in response to a constant concentration of a threshold number of molecules within the molecule cushions 212. For example, if the reserve concentrations of fewer than 10 molecules are used from the molecule cushions 212, the simulation engine 108 may increase the simulation time step 310, for example from one second to two seconds.

As one example of how this increase may be calculated, two separate parallel runs of the simulation may be performed where each parallel run uses a different time step. As an example, time step $t_s$ for the first run may be run for a single time step, and example time step $t_s 2$ may be run for two time steps. The results of these parallel runs may be compared to evaluate where the state or simulation data of the model is sufficiently similar within a threshold between the two runs. If they are sufficiently similar, then the shorter time step may be used as it may better represent the amount of time it takes information to propagate through the simulated system.

Alternatively, an increased time step allows for fewer calculations during a simulation. Thus, as the throughput of molecules within sub-models of a whole cell model remains stable, the simulation time step 310 may be increased to reduce computation associated with simulation of the whole cell model.

In some examples, the simulation time step 310 is decreased in response to molecule concentrations within sub-models dipping below a threshold between previous time steps. In some examples, the simulation time step 310 may be decreased in response to a molecule's net concentration across all sub-models of a whole cell model falling below a threshold. In some examples, the simulation time step 310 may be decreased in response to a change in the concentration of a threshold number of molecules within the molecule cushions 212. For example, if the reserve concentrations of more than 15 molecules are used from the molecule cushions 212, the simulation engine 108 may decrease the simulation time step 310, for example, from 1 second to half a second. A similar parallel run process as described above may be used to determine whether to change the time step. In some examples, the simulation time step 310 may be decreased in response to use of a single molecule within the molecule cushions 212. Decreasing the simulation time step 310 increases the number of calculations associated with the simulation of a whole cell model, however it also allows for more adjustments of the distribution of molecules across sub-models during a simulation, as described in further detail below. The decrease in simulation time steps 310 may thus prevent conflicts for molecules between sub-models, and the full depletion of a molecule in the whole cell model.

The simulation time step 310 is stored in the state dataset 302, and conveyed to the sub-models by the state dataset 302. If the simulation time step 310 is dynamic, the state dataset 302 communicates the updated simulation time step 310 value to the sub-models after each iterative solution of the whole cell model. The simulation time step 310 may be adjusted by the simulation engine 108 of the computer simulation system 100, as shown in FIG. 1.

V. PER-MOLECULE COMPONENTS

For each molecule entry within the molecules 304, a number of per-molecule metrics are stored. As an example, the metrics stored within molecule$_1$ 306a are illustrated in FIG. 3. It is to be understood that the metrics described with reference to molecule$_1$ 306a are also stored for each of the molecules within molecules 304, such as molecule$_2$ 306b through molecule$_N$ 306c.

A. Units

The solutions to a whole cell model may be converted to any number of units 312. For example, as a result of the solutions to FBA metabolism, a metabolic sub-model may produce flux values of molecules into and out of the metabolic sub-model. While the flux values are the initial solutions produced by the FBA formulation of the metabolic sub-model, flux values may be converted to a number of other units, such as net concentration of a molecule within metabolism, pH levels produced by the molecule, moles of a molecule, etc. Depending on the mathematical framework of a sub-model, different units may be more useful than others. For example, if a sub-model contains a mass balance requirement, the mass associated with a molecule in the sub-model may be a more useful metric than a pH level. For each molecule, the state dataset 302 contains a number of different units 312 in which to convert the solutions and conditions of a molecule in the whole cell model. Units 312 may be any of the International System of Units (SI Units). For example, unit$_1$ 314a may be mass, unit$_2$ 314b may be moles, and unit$_N$ 314c may be a concentration such as grams/mL. Any of the units 312 may be selected for each of the molecules 304. For example, molecule$_1$ 306a may be stored within the state dataset 302 with metrics converted to unit$_1$ 314a, while molecule$_2$ 306b may be stored within the state dataset 302 with metrics converted to unit$_2$ 314b. In other examples, all molecules 304 may be stored within the state dataset 302 with metrics in the same unit of units 312.

B. Aggregate Metrics

Once a unit from units 312 is selected, the metrics 315 are converted to the selected unit. For example, as shown in FIG. 3, the metrics 315 for molecule$_1$ 306a are converted to be expressed in unit$_1$ 314a. Any of the units 312 may be selected, and unit$_1$ 314a is shown as an example. Metrics 315 are stored within the state dataset 302 for each molecule in the molecules 304. The metrics include aggregate metrics collected for each molecule across all sub-models of a whole cell model. The aggregate metrics include net value 316 (shown in FIG. 3 as being expressed in unit$_1$ 314a), a net uprate 318 (expressed in unit/time) and a net downrate (unit/time) 320. The net value 316 measures the instantaneous amount on hand of a molecule within a whole cell model at any given time step of a simulation. For example, the net value 316 may give the net number of molecules' 306a within a whole cell model. The net value 316 is aggregated for a single molecule (molecule$_1$ 306a) across all sub-models of a whole cell model. The aggregate metrics also include a net uprate 318, shown in FIG. 3 as expressed in unit/time. The net uprate 318 measures the net demand for molecule$_1$ 306a across all sub-models of a whole cell model. The net uprate 318 thus gives an instantaneous rate of consumption of a molecule across all sub-models of a whole cell model. Similarly, the aggregate metrics include a net downrate 320 across all sub-models of a whole cell model. The net downrate 320 measures the net supply for molecule$_1$ 306a across all sub-models of a whole cell model. The net downrate 320 thus gives an instantaneous rate of production of a molecule across all sub-models of a whole cell model. The aggregate metrics (net value 316, net uprate 318 and net downrate 320) describe the aggregate state of a molecule within the whole cell model.

The aggregate metrics are conveyed by the state dataset 302 to all sub-models 336 as the whole cell model outcome 334 of a time step of a simulation. Thus after each time step, the simulation is solved and the aggregate metrics determined. Before the next time step is calculated, all sub-models 336 receive the whole cell model outcome 334, which includes the net value 316, the net uprate 318 and the net downrate 320 expressed in terms of the selected unit from the units 312. This is described in further detail with reference to FIG. 4. All sub-models 336 are thus able to "see" the aggregate state of each molecule across all other sub-models. Additional local metrics 315 are also conveyed by the state dataset 302 to the sub-models, as described in further detail below.

C. Local Metrics

The metrics 315 for each of the molecules 304 stored in the state dataset 302 also include local metrics, which measure the state of a molecule in the local environment of a sub-model of the whole cell model. Similarly to the aggregate metrics, the local metrics are expressed according to a selected unit. For example, the local metrics are shown in FIG. 3 expressed in terms of the selected unit$_1$ 314a. The local metrics include the sub-model$_1$ value 322, which measures the instantaneous amount on hand of a molecule within a sub-model. The local metrics also include both uprates and downrates for each sub-model, which measure the instantaneous rate of change of a molecule within a sub-model. As shown in FIG. 3, the local metrics measure a sub-model$_1$ uprate 324, shown in FIG. 3 as expressed in unite/time. The sub-model$_1$ uprate 324 measures the net demand for molecule$_1$ 306a within the local environment of sub-model$_1$. The net uprate 318 thus gives an instantaneous rate of consumption of a molecule within a single sub-model. Similarly, the aggregate metrics include a sub-model$_1$ downrate 326 within the local environment of sub-model$_1$. The sub-model$_1$ downrate 326 measures the supply of molecule$_1$ 306a within sub-model$_1$. The sub-model$_1$ downrate 326 thus gives an instantaneous rate of production of a molecule within a single sub-model. The local metrics (sub-model$_1$ value 322, sub-model$_1$ uprate 324 and sub-model$_1$ downrate 326) describe the local state of a molecule within a single sub-model. The local metrics are stored in the state dataset 302 and determined for each of the molecules 304 and for each sub-model, and are expressed in the selected unit. Thus, if a whole cell model contains M sub-models, the state dataset 302 includes local metrics for each of the M sub-models. The local metrics for sub-model M are shown in FIG. 3 as the sub-model$_M$ value 328, the sub-model$_M$ uprate 330 and the sub-model$_M$ downrate 332.

The local metrics for each sub-model are conveyed to their corresponding sub-models in addition to the whole cell model outcome 334. Thus after each time step, the simulation is solved and the local metrics determined. Before the next time step is calculated, each sub-model receives their corresponding local sub-model outcome. This is described in further detail with reference to FIG. 4. All sub-models 336 are thus able to "see" the local state of each molecule within themselves, but are not given access to the local state of molecules within other sub-models. Thus the sub-model outcome 324 includes the sub-models value 322, the sub-model$_1$ uprate 324 and the sub-models downrate 326, which are conveyed together to the corresponding sub-models 338. Similarly, the local metrics for sub-model M 340 are conveyed to sub-model M as the sub-model outcome 344, which includes the sub-model$_M$ value 328, the sub-model$_M$ uprate 330, and the sub-model$_M$ downrate 332. However, the only "knowledge" sub-models 338 has of the local state within sub-model M 340 is through the aggregate metrics it receives as the whole cell model outcome 334, which include the local state of sub-model M 340 in combination with all other sub-models.

The metrics 315, whole cell model outcome 334, and each individual sub-model outcomes (such as sub-model outcome 342 and sub-model outcome 344) are updated after each time step following iterative solutions to a whole cell model. Based on the received whole cell model outcome 334 and its local outcome, each sub-model determines its local production and consumption of each of the molecules 304. Thus molecules 304, which are common to all sub-models, are distributed among the sub-models of a whole cell model based on the outputs of the state dataset 302. This is described in further detail below.

VI. STATE DATASET IN A TIME SERIES

Figure 4:
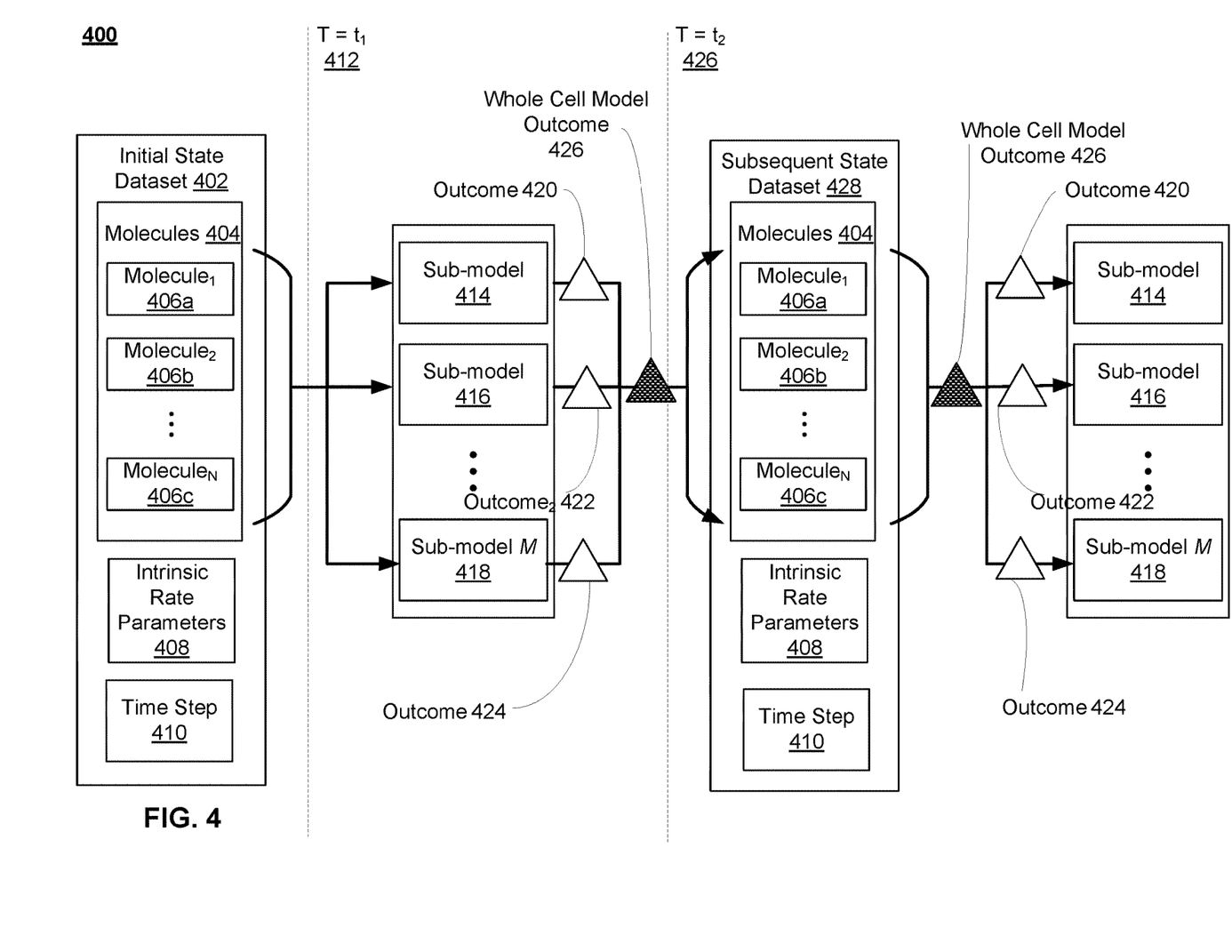
FIG. 4 is a block diagram of a time series using a coordinating state dataset, according to one embodiment.

FIG. 4 is a block diagram of a time series 400 using a coordinating state dataset, according to one embodiment. The state dataset is structured as the state dataset 302, and contains the elements described with reference to FIG. 3. The time series 400 produces a simulation of a whole cell model. Three time steps at $t_1$ 412, $t_2$ 426, $t_3$ 430 are shown in FIG. 4 as examples, however it is to be understood that a simulation of the whole cell model may be divided between any number of time steps.

A. Initialization

The values within the initial state dataset 402 are initialized before proceeding through the time series 400. Thus each molecule within the molecules 404 is given an initial value for each of the metrics 315 as described with reference to FIG. 3. For example, molecule$_1$ 306a is given an initial net value 316, an initial net uprate 318, an initial net downrate 320, and initial local metrics. For example, each of the local metrics for each of the sub-models is given an initial sub-model value (such as the sub-model$_1$ value 316) an initial sub-model uprate (such as the sub-model$_1$ uprate 324) and an initial sub-model downrate (such as the sub-model$_1$ downrate 326). The initial values assigned to each molecule in the molecules 404 represent the initial conditions of a cell before a simulation of the whole cell is determined.

In addition to initializing metrics associated with each molecule, the initial state dataset 402 includes an initial time step 410. As discussed with reference to FIG. 3, the time step 410 may be changed during the time series 400. The intrinsic rate parameters 408 are also initialized, however these values remain constant throughout the simulation 400.

B. First Time Step

Based on the initialized metrics 315, the initial state dataset 402 provides each sub-model of a whole cell model with global metrics for each molecule in the molecules 404, which are determined from the initialized net value 316, initialized net uprate 318, and initialized net downrate 320. As described in FIG. 3, the global metrics are provided to each sub-model in the whole cell mode. Each sub-model also receives from the initial state dataset 402 their respective local metrics, which are determined from an initialized sub-model value, an initialized sub-model uprate, and an initialized sub-model downrate. The initial state dataset 402 further communicates to each sub-model the intrinsic rate parameters 408 and the initialized time step 410. Thus sub-model 414 receives global metrics and the local metrics for sub-model 414.

Solutions to the whole cell model are then determined given the values provided in the initial state dataset 402. Each of the sub-models in the whole cell model produces a sub-model outcome, which is the solutions to the sub-model. For example, if a sub-model is based on FBA, the outcome of the sub-model may be the flux value solutions to the FBA equations given the input values from the initial state dataset 402. Thus sub-model 414 produces outcome 420, sub-model 416 produces outcome 422, and sub-model M produces outcome 424.

The sub-model outcomes are determined from the global metrics and the local metrics. A given sub-model's outcome, therefore, is based on information about the aggregate state of molecules and the local state of molecules of that sub-model. Thus the production and consumption of molecules with each sub-model is determined given the sub-model's past behavior (the initial local metrics provided by the initial state dataset 402) and the aggregate conditions outside of the sub-model (the global metrics provided by the initial state dataset 402).

The individual outcomes from each of the sub-models are combined to determine the whole cell model outcome 426. For examples, each of the outcomes may be added together to produce the whole cell model outcome 426.

C. Second Time Step

The individual outcomes from each of the sub-models and the whole cell model outcome 426 as solved at the first time step $t_1$ 412 are all conveyed to the subsequent state dataset 428 at the second time step $t_2$ 426. Based on the outcomes from each of the sub-models and the whole cell model outcome 426, the initial state dataset 402 is updated to produce the subsequent state dataset 428. Thus each of the initialized metrics are re-calculated given the whole cell model outcome 426 and each of the sub-model outcomes. For example, molecule$_1$ 406a may have a different net value 316, net uprate 318 and net downrate 320 following the first time step of the time series 400. The metrics for each molecule in the molecules 404 are re-calculated. The intrinsic rate parameters 408 remain constant. If, as described with reference to FIG. 2, a molecule concentration is depleted, the time step 410 may be decreased at $t_2$ 426. In some examples, the time step 410 may be increased.

The subsequent state dataset 428 then conveys the whole cell model outcome 426 determined from the subsequent state dataset 428 to each of the sub-models in the whole cell model, in addition to the local outcomes for each respective sub-model. For example, outcome 420 is communicated to sub-model 414, outcome 422 is communicated to sub-model 416 and outcome 424 is communicated to sub-model M 418. Based on these metrics, the solutions to each of the sub-models are determined for the second time step $t_2$ 426.

This process may be repeated for any number of time steps, as the state dataset is iteratively updated given the solutions to a previous time step and the relevant metrics conveyed to sub-models for subsequent time steps.

VII. METHOD OVERVIEW

Figure 5:
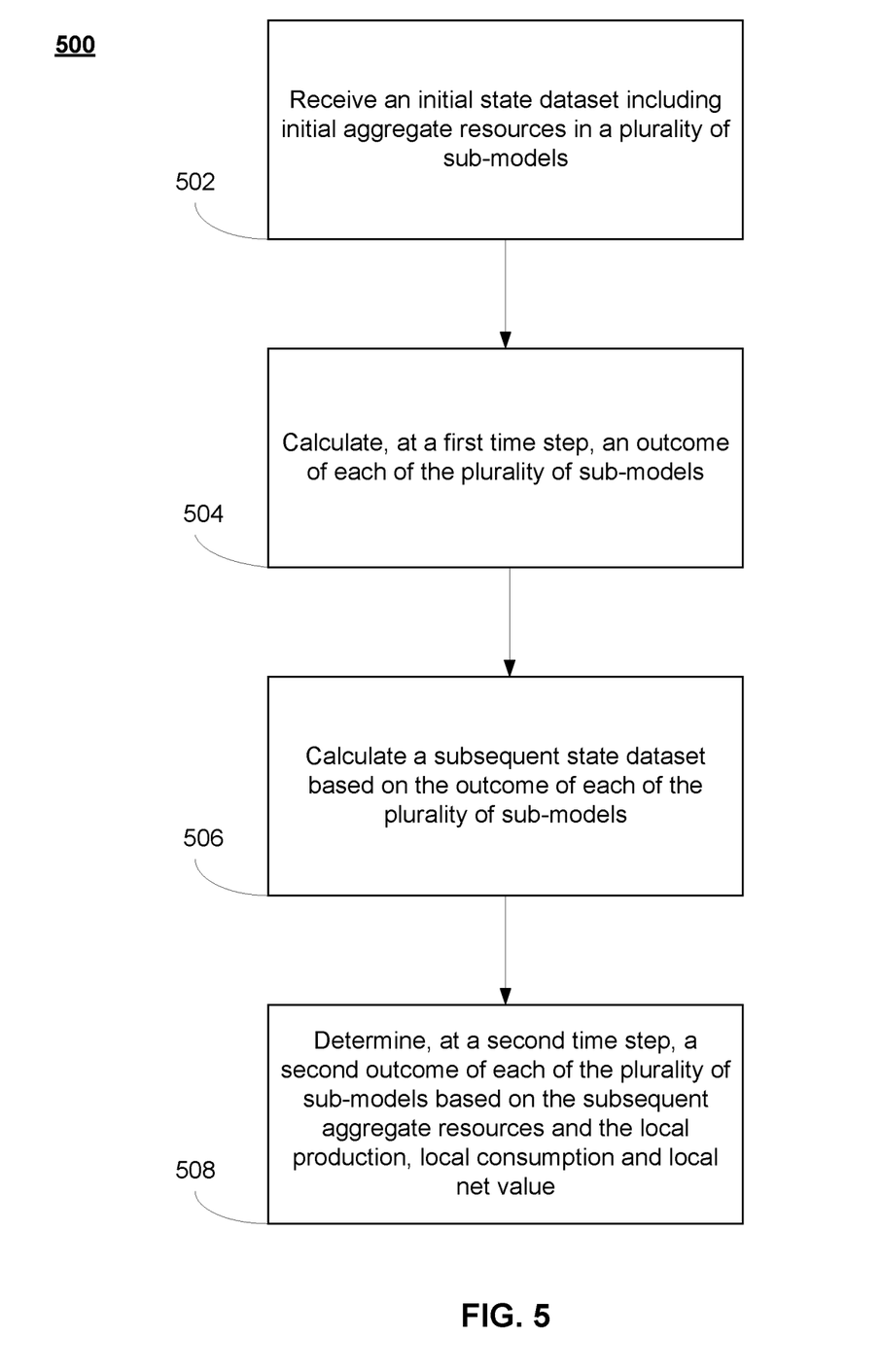
FIG. 5 is a flowchart for a method for allocating resources among multiple sub-models in a simulation of a biological cell, according to one embodiment.

FIG. 5 is a flowchart 500 for a method for allocating resources among multiple sub-models in a simulation of a biological cell, according to one embodiment. The method may be executed by the computer simulation system 100, and more specifically by the simulation engine 108. The simulation engine 108 receives 502 an initial state dataset including initial aggregate resources in a plurality of sub-models. The initial state dataset may be the initial state dataset 402 as described with reference to FIG. 4. As described herein, the aggregate resources may be the net value 316, the net uprate 318 and the net downrate 320 that together make up the whole cell model outcome. The aggregate resources may be determined and stored within the initial state dataset 402 for each molecule in the molecules 304.

The simulation engine 108 calculates 504, at a first time step, an outcome of each of the plurality of sub-models. This may be the first time step $t_1$ 412 as described in further detail with reference to FIG. 4. The plurality of outcomes may be the local metrics for each sub-model, including the sub-model value (such as sub-models value 322), the sub-model uprate (such as the sub-models uprate 324) and the sub-model downrate (such as the sub-models downrate 326). The outcome of each of the plurality of sub-models may be determined and stored in a state dataset for each molecule in the molecules 304.

The simulation engine 108 calculates 506 a subsequent state dataset based on the outcome of each of the plurality of sub-models. This may be the subsequent state dataset 428 as described in further detail with reference to FIG. 4. The outcome of each of the plurality of molecules may be the outcomes 420, 422 and 424 as shown in FIG. 4. The subsequent state dataset is thus updated from the initial state dataset of a previous time step.

The simulation engine 108 determines 508, at a second time step, a second outcome of each of the plurality of sub-models based on the subsequent aggregate resources and the local production, local consumption and local net value. The subsequent aggregate resources may be the whole cell model outcome 426. The local production, local consumption and local net value may be the sub-model value, sub-model uprate and sub-model downrate, respectively. Thus the local production, local consumption and local net value are the sub-model outcomes (such as the outcomes 432, 434 and 436), which reflect the local state of molecules within a single sub-model. The second time step may be the time step $t_2$ 426 as shown in FIG. 4.

VIII. ADDITIONAL CONSIDERATIONS

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A computer-implemented method comprising:
   receiving, at a state dataset, an initial state dataset for performing a simulation of a biological cell using a whole cell model, wherein the whole cell model comprises a plurality of sub-models that transfer molecules and resources based on production and consumption of the molecules within each sub-model, and the initial state dataset includes, for each molecule, a corresponding molecule entry, the molecule entry including initial aggregate metrics of the molecule in the whole cell model and initial local metrics of the molecule for each sub-model;
   communicating, by the state data set, at a first time step of the simulation, to each sub-model, the initial aggregate metrics of the molecules in the whole cell model and the initial local metrics of the molecules for the sub-model;
   calculating, by each sub-model at the first time step, a first sub-model outcome based on the initial aggregate metrics of the molecules in the whole cell model and the initial local metrics of the molecules for the sub-model;
   combining, at the first time step, the first sub-model outcomes for the plurality of sub-models to determine a whole cell model outcome;
   receiving, at the state dataset at a second time step from each sub-model, the first sub-model outcome calculated by each sub-model, wherein each sub-model does not communicate the first sub-model outcome to other sub-models of the plurality of sub-models;
   updating, by the state dataset, the initial state data set to generate a subsequent state dataset based on the first sub-model outcome of each sub-model and the whole cell model outcome, wherein the subsequent state dataset includes, for each molecule, the corresponding molecule entry, the molecule entry including updated aggregate metrics of the molecule in the whole cell model and updated local metrics of the molecule for each sub-model;
   communicating, by the state data set, at the second time step of the simulation, to each sub-model, the updated aggregate metrics of the molecules in the whole cell model and the updated local metrics of the molecules for the sub-model;
   calculating, by each sub-model at the second time step, a second sub-model outcome based on the updated aggregate metrics of the molecules in the whole cell model and the updated local metrics of the molecules for the sub-model;
   combining, at the second time step, the second sub-model outcomes for the plurality of sub-models to determine an updated whole cell model outcome; and
   determining simulation data reflective of the simulation of the biological cell based on the first outcome and the second outcome.

2. The method of claim 1, wherein the initial state dataset further includes:
   a set of intrinsic rate parameters for each molecule, wherein the set of intrinsic rate parameters represents a biological ability of the biological cell to adjust the second sub-model outcome of each sub-model to the first sub-model outcome of each sub-model.

3. The method of claim 2, wherein the set of intrinsic rate parameters for each molecule includes a proportional rate limit, an integral rate limit, a derivative rate limit, or a combination thereof.

4. The method of claim 1, wherein:
   the updated local metrics comprise an updated sub-model net value, an updated sub-model uprate, and an updated sub-model downrate;
   the updated local metrics represent conditions of the biological cell after performing the first time step of the simulation; and
   the updated local metrics are determined from a mass balance constraint.

5. The method of claim 1, further comprising:
   performing a wet lab analysis with a plurality of cells of a same type as the biological cell of the simulation, wherein the wet lab analysis comprises a parameter space defined by the simulation data.

6. A non-transitory computer readable storage medium storing a plurality of instructions executable by one or more processors, the plurality of instructions comprising instructions that when executed by the one or more processors cause the one or more processors to perform processing comprising:
   receiving, at a state dataset, an initial state dataset for performing a simulation of a biological cell using a whole cell model, wherein the whole cell model comprises a plurality of sub-models that transfer molecules and resources based on production and consumption of the molecules within each sub-model, and the initial state dataset includes, for each molecule, a corresponding molecule entry, the molecule entry including initial aggregate metrics of the molecule in the whole cell model and initial local metrics of the molecule for each sub-model;

communicating, by the state data set, at a first time step of the simulation, to each sub-model, the initial aggregate metrics of the molecules in the whole cell model and the initial local metrics of the molecules for the sub-model;

calculating, by each sub-model at the first time step, a first sub-model outcome based on the initial aggregate metrics of the molecules in the whole cell model and the initial local metrics of the molecules for the sub-model;

combining, at the first time step, the first sub-model outcomes for the plurality of sub-models to determine a whole cell model outcome;

receiving, at the state dataset at a second time step from each sub-model, the first sub-model outcome calculated by each sub-model, wherein each sub-model does not communicate the first sub-model outcome to other sub-models of the plurality of sub-models;

updating, by the state dataset, the initial state data set to generate a subsequent state dataset based on the first sub-model outcome of each sub-model and the whole cell model outcome, wherein the subsequent state dataset includes, for each molecule, the corresponding molecule entry, the molecule entry including updated aggregate metrics of the molecule in the whole cell model and updated local metrics of the molecule for each sub-model;

communicating, by the state data set, at the second time step of the simulation, to each sub-model, the updated aggregate metrics of the molecules in the whole cell model and the updated local metrics of the molecules for the sub-model;

calculating, by each sub-model at the second time step, a second sub-model outcome based on the updated aggregate metrics of the molecules in the whole cell model and the updated local metrics of the molecules for the sub-model;

combining, at the second time step, the second sub-model outcomes for the plurality of sub-models to determine an updated whole cell model outcome; and determining simulation data reflective of the simulation of the biological cell based on the first outcome and the second outcome.

7. The computer readable medium of claim 6, wherein the initial state dataset further includes:

a set of intrinsic rate parameters for each molecule, wherein the set of intrinsic rate parameters represents a biological ability of the biological cell to adjust the second sub-model outcome of each sub-model to the first sub-model outcome of each sub-model.

8. The computer readable medium of claim 7, wherein the set of intrinsic rate parameters for each molecule includes a proportional rate limit, an integral rate limit, a derivative rate limit, or a combination thereof.

9. The computer readable medium of claim 6, wherein:

the updated local metrics comprise an updated sub-model net value, an updated sub-model uprate, and an updated sub-model downrate;

the updated local metrics represent conditions of the biological cell after performing the first time step of the simulation; and the updated local metrics are determined from a mass balance constraint.

10. The computer readable medium of claim 6, further comprising:

performing a wet lab analysis with a plurality of cells of a same type as the biological cell of the simulation, wherein the wet lab analysis comprises a parameter space defined by the simulation data.

* * * * *